United States Patent [19]

Zaiger et al.

[11] Patent Number: Plant 7,090

[45] Date of Patent: Jan. 2, 1990

[54] INTERSPECIFIC TREE "FLAVOR DELIGHT"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 302,795

[22] Filed: Jan. 23, 1989

[51] Int. Cl.[4] ..... A01H 5/00

[52] U.S. Cl. ..... Plt./39

[58] Field of Search ..... Plt./38, 39

*Primary Examiner*—James R. Feyrer

[57] ABSTRACT

An interspecific (Apricot×Plum Cot) tree which is of large size, vigorous, medium dense, semi-upright growth and a regular and productive bearer of early maturing, medium size, yellow flesh, freestone fruit. The skin color of the fruit has the appearance of an apricot although slightly duller yellow color. The flesh characteristic is typical apricot flesh near the pit cavity which becomes firmer and somewhat crisp as the distance toward the skin increases, this firm flesh characteristic holds the fruit shape when fully tree ripe and the canned fruit halves also maintain the attractive upright appearance after processed. The fruit is further characterized by having a good balance between acid and sugar giving it an excellent flavor with a lingering aftertaste. The delicate aftertaste is detected in both the fresh and the canned fruit, although somewhat stronger in the fresh fruit. The soluble solids (Brix) average is approximately 4 degrees higher than most commercially grown apricots in California.

1 Drawing Sheet

ORIGIN OF THE VARIETY

The present new and distinct variety of interspecific tree was originated by us in the experimental orchard located near Modesto, Calif., as a first generation seedling from a cross between Modesto Apricot (U.S. Plant Pat. No. 2,543) and a plum cot selection. The plum cot selection, which was the pollen parent, originated from seed of an open pollinated Red Beaut Plum (U.S. Plant Pat. No. 2,539). A large group of these first generation seedlings were planted and grown under careful observation by us, gave many and varying characteristics, one such seedling which is the present interspecific variety, having been especially desirable with respect to its excellent fruit quality and flavor, was selected for asexual reproduction and commercialization.

ASEXUAL REPRODUCTION OF THE VARIETY

The present variety of interspecific tree was asexually reproduced by budding in our experimental orchard located at Modesto, Calif. and shows that the unique characteristics of the new variety come true to form and are established and transmitted through succeeding propagations.

DESCRIPTION OF THE PHOTOGRAPHS

The accompanying color photographs show typical specimens of the fruit and foliage of our new variety with upper and lower surface of the foliage being illustrated and the exterior and a cross sectional view of the fruit divided in its suture plane to reveal flesh coloration and showing a stone remaining in place. The illustrations were taken shortly after being picked at maturity, (firm ripe) and the colors are as nearly true as is reasonably possible in a color representation of this type.

SUMMARY OF THE VARIETY

The new and distinct variety of interspecific tree (Apricot×Plum Cot) is of large size, vigorous, semi-upright growth and a productive and regular bearer of medium size, yellow flesh, freestone fruit. The present variety of interspecific tree grows similar to an apricot tree and when compared to its seed parent, Modesto Apricot Tree (U.S. Plant Pat. No. 2,543) has a more rough bark condition throughout the tree, has flowers that are similar in size, shape and color although greater in number with more profuse bloom; has fruit which are duller yellow in skin color and approximately 4 degrees higher in soluble solids (Brix). The flavor of the interspecific fruit is excellent, predominately apricot but suggestive of plum with a lingering aftertaste both in the fresh and the canned fruit.

DESCRIPTION OF THE VARIETY

The botanical description of this new and distinct variety of interspecific tree, its foliage and fruit are based on observations of specimens grown at Modesto, Calif., with color terminology (except those in common terms) referenced to Reinhold Color Atlas by A. Kornerup and J. H. Wanscher are as follows.

Tree:
- *Size.*—Large.
- *Vigor.*—Vigorous.
- *Density.*—Medium dense.
- *Form.*—Semi-upright.
- *Production.*—Productive.
- *Bearing.*—Regular.

Trunk:
- *Size.*—Stocky.
- *Surface.*—Shaggy-rough.
- *Color.*—Grayish brown.

Branches:
- *Size.*—Medium, stocky.
- *Lenticels.*—Medium number. Large.
- *Texture.*—Medium rough.
- *Color.*—New growth — reddish brown. Old growth — brown to grayish brown.

Leaves:
- *Size.*—Medium. Average length — 2¼" to 3". Average width — 1⅞" to 2¼".
- *Form.*—Ovate.

*Thickness.*—Medium.
*Margin.*—Serrate.
*Petiole.*—Average length — $\frac{7}{8}$". Average width — 5/64".
*Glands.*—Average number 1, range 0–3. Located on base of leaf and upper portion of petiole.
*Color.*—Upper surface — green (28-E-7) to (28-E-8). Lower surface — grayish green (28-E-5) to (28-E-6).

Flower buds:
*Size.*—Medium.
*Shape.*—Medium.

Flowers:
*Blooming period.*—Feb. 22, 1985 to Mar. 2, 1985. Varies slightly due to weather variations.
*Size.*—Large.
*Color.*—Pink—fades to white at petal fall.
*Pubescent.*—Present.

Fruit:
*Maturity when described.*—Firm ripe.
*Date of first picking.*—June 15, 1985.
*Date of last picking.*—June 22, 1985.
*Size.*—Medium. Axial diameter — 1 15/16". Transverse diameter in suture plane — $1\frac{7}{8}$". Diameter measured at right angles to suture plane — $1\frac{5}{8}$".
*Form.*—Usually symmetrical. Globose. Usually more round at right angles to suture plane than most apricots.
*Suture.*—Extends from base to apex. Terminates at blossom end. A slightly darker skin color line on most fruit.
*Cavity.*—Round to slightly enlongated in suture plane. Depth — $\frac{1}{4}$" to $\frac{3}{8}$". Breadth — $\frac{3}{8}$" to $\frac{1}{2}$".
*Apex.*—Rounded to slightly depressed.

Skin:
*Thickness.*—Medium.
*Tendency to crack.*—None.
*Down.*—Moderate. Short.
*Tenacity.*—Tenacious to flesh.
*Color.*—Brownish yellow (5-C-7) to brownish orange (6-C-7).

Flesh:
*Flavor.*—Excellent. Predominately apricot but suggestive of plum. Lingering aftertaste.
*Juice.*—Moderate.

*Fibers.*—Few — small. Tender.
*Texture.*—Predominately apricot next to pit cavity—becomes firmer as distance advances toward skin.
*Ripens.*—Evenly.
*Eating quality.*—Excellent.
*Color.*—Melon yellow (5-A-6) to golden orange (5-B-8).

Stone:
*Type.*—Free. Adheres very slightly to flesh along ventral edge and stone cavities in some fruit.
*Size.*—Medium. Average length — $\frac{7}{8}$". Average breadth — $\frac{3}{4}$". Average thickness — $\frac{1}{2}$".
*Form.*—Ovid. Base — varies from round to straight apex — usually round — very slight tip on some stones.
*Tendency to split.*—None.
*Surface.*—Slightly pitted throughout. Slight ridges extending across surface of the stone on both sides of suture plane.
*Color.*—Varies slightly from light brown (5-E-6) to brown (5-F-6).

Use: Dessert. Market. Culinary.
Keeping quality: Good.
Shipping quality: Fair to good.

The interspecific tree and its fruit herein described may vary in slight detail due to climatic and soil conditions under which the variety may be grown; the present botanical description being that of the variety grown at Modesto, Calif.

We claim:

1. A new and distinct variety of interspecific (Apricot×Plum Cot) tree substantially as illustrated and described, characterized by its large size, vigorous growth and a regular and productive bearer of medium size, yellow flesh, freestone fruit, with a good balance between acid and sugar giving it excellent flavor and eating quality; the fruit is further characterized by having typical apricot flesh near the pit cavity which becomes firmer as the distance toward the skin increases, this firm flesh characteristic holds the fruit shape when fully tree ripe and the canned halves also maintain the attractive upright appearance after being processed.

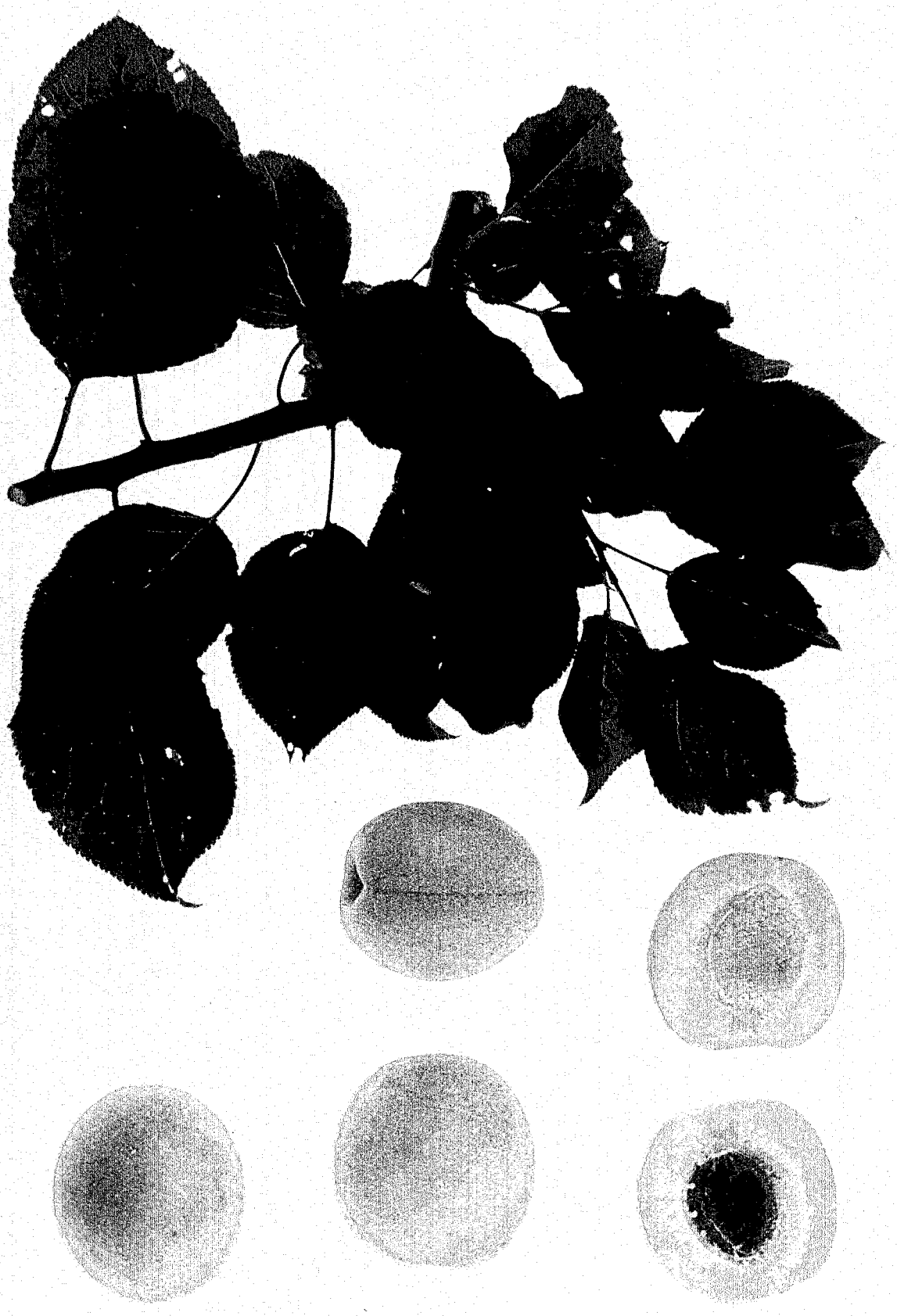

* * * * *